United States Patent [19]

Catoul

[11] 4,003,260
[45] Jan. 18, 1977

[54] APPARATUS FOR TESTING MOLTEN METAL

[75] Inventor: Philippe Felix Catoul, Horion-Hozemont, Belgium

[73] Assignee: Centre de Recherches Metallurgiques-Centrum voor Research in de Metallurgie, Brussels, Belgium

[22] Filed: Nov. 25, 1974

[21] Appl. No.: 526,687

[30] Foreign Application Priority Data

Nov. 27, 1973 Belgium .............................. 807880

[52] U.S. Cl. ........................ 73/423 R; 33/126.4 R; 73/425.4 R; 73/DIG. 9; 116/109; 116/118 R
[51] Int. Cl.² ..................... G01F 23/00; G01N 1/10
[58] Field of Search .......... 73/422, 425.4 R, 425.6, 73/423 R, 432 HA, 421 R, DIG. 9; 116/106, 68, 109, 114.5, 118 R, DIG. 7; 33/126.4 R

[56] References Cited

UNITED STATES PATENTS

| 2,620,815 | 12/1952 | Margraf et al. ..................... 116/106 |
| 3,153,345 | 10/1964 | Berg ................................. 73/423 R |
| 3,313,159 | 4/1967 | Vanderbeck ..................... 73/423 R |
| 3,559,452 | 2/1971 | Perbix et al. ............. 73/425.4 R X |
| 3,577,886 | 5/1971 | Wiese ............................ 73/425.4 R |
| 3,724,276 | 4/1973 | Schwind ...................... 73/423 R X |
| 3,853,009 | 12/1974 | Sutherland ........................ 73/423 R |

Primary Examiner—Richard E. Aegerter
Assistant Examiner—Richard R. Stearns
Attorney, Agent, or Firm—Holman & Stern

[57] ABSTRACT

A measuring or sampling probe is to be lowered to a desired depth in a molten metal. The probe is mounted on a probe carrier which can be lowered and raised. A contact detector, which emits a control signal when the detector comes into contact with the upper surface of the molten metal, is fixed on the probe carrier at a distance above the probe.

5 Claims, 4 Drawing Figures

APPARATUS FOR TESTING MOLTEN METAL

This invention relates to an apparatus for testing molten metal by lowering a measuring or sampling probe to a desired depth in the metal.

Efficient control of the development of a metallurgic process depends, among other things, upon the knowledge of various parameters which are characteristic of the state of the metal being processed; when these parameters are measured, this should be done as accurately as possible and in the shortest possible time. In particular, as far as steel processing is concerned, the parameters to be considered are the temperature, the composition, and the oxygen activity of the steel.

It is also apparent that the rapidity with which the results of the measurements made are obtained determines the time within which it is possible to intervene or to take all suitable measures capable of ensuring the completion in the desired way of the metallurgic operation concerned. This delay time not only affects the productivity of the process being carried out but also the magnitude of the reactions.

On the other hand, the dispersion of the results of the measurements carried out depends on the reproducibility of the conditions under which these measurements are carried out.

Until recently, the drawing of samples from a ladle was carried out by an operator who sank a probe into the ladle, the probe being capable of picking up a sample.

The above procedure does not apparently ensure conditions always identical from the viewpoint of the probe position, penetration depth, immersion duration, etc.

With the above method, since the human factor plays an important role, the reproducibility of the operating conditions is highly aleatory, which makes it difficult to interpret the results of the measurements and the corrections to be made in order to be sure that all possible differences in the operating conditions of the measurements themselves are taken into account.

To eliminate these drawbacks, it has already been suggested, in the case of measurements to be made on molten steel in a ladle, to employ a measurement probe whose sinking movement is of a constant amplitude and is controlled by an electrical control. Much of the influence of the human factor was expected to be eliminated in this way. However, the use of this improved arrangement has not allowed really identical and reproducible operating conditions to be obtained. Indeed, depending upon whether the ladle has a new or a worn out lining and whether it is filled to a greater or lesser extent, the probe (whose movement amplitude is contant) is immersed to a greater or lesser extent into the molten metal. The extent to which the probe penetrates into the molten steel varies then from one operation to another. The same applies to the dwell time of the probe in contact with the steel.

The present invention provides an apparatus for testing molten metal by lowering a measuring or sampling probe to a desired depth in the molten metal, the apparatus comprising a probe, a probe carrier, means for lowering and raising the probe carrier, and a contact detector which emits a control signal when the detector comes into contact with the molten metal, the detector being fixed on the probe carrier at a distance above the probe.

Preferably, the lowering of the probe is stopped automatically by stopping means actuated by the control signal. The arrangement should be such that the probe reaches the desired depth at the end of the dead time between emission of the signal and stopping of descent.

The signal emitted by the contact detector may for example, be an electric or sonic signal; the best results, however, are obtained with a pneumatic signal, since in this case a particularly simple and cheap device easy to manufacture and to replace may be used as a contact detector.

The contact detector may be advantageously a hollow body or ferrule of cardboard (or other combustible material) mounted on a tube rigid with the probe carrier, the hollow body starting to burn upon coming into contact with the upper surface of the molten metal. The gases produced by this combustion create a pressure in the ferrule and the tube (i.e. a pneumatic signal) which pressure results in a diaphragm being displaced to actuate means for stopping the descent of the probe.

In practice, the distance between the end of the probe and the end of the contact detector is slightly smaller than the depth desired because the dead time between the moment in which the contact detector emits its signal and that in which the probe is actually stopped must be taken into account. During this dead time, the probe falls a distance which is a function of the speed at which it is being lowered. The adjustment of the actual distance between the end of the probe and that of the contact detector is made by trials and by taking into account factors such as those mentioned above, so that the head of the probe actually stops at the desired depth below the upper surface of the molten metal.

The apparatus preferably comprises an automatic control assembly which allows the probe to be lowered to the desired depth, to dwell at this depth for a predetermined time period, and to be withdrawn from the molten metal.

Figure 1:
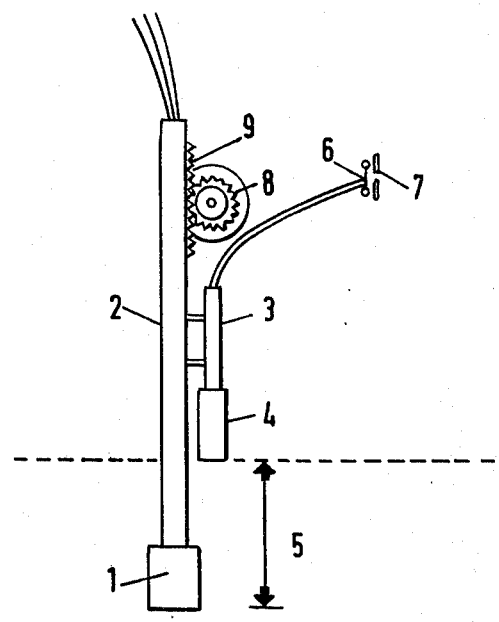
FIG. 1 illustrates the measuring and/or sampling probe of the invention.

The testing device illustrated in FIG. 1 comprises a measuring and/or sampling probe 1 located at the end of a probe carrier 2. A hollow tube 3 attached to the probe carrier 2 carries a cardboard ferrule 4 at its lower end, this ferrule being hollow and secured to the tube 3. The distance 5 between the end of the probe 1 and that of the ferrule 4 is such that the head of the probe, when immersed substantially vertically into the molten metal, reaches a desired depth as the ferrule 4 enters the metal.

At the moment when, during the descent of the probe, the end of the ferrule 4 reaches the upper surface of the molten metal, the resulting gases produced by the combustion of the ferrule create a local pressure which propagates through the ferrule and the hollow tube 3 up to a flexible diaphragm 6 which actuates a micro-switch 7 controlling the automatic stopping of a motor which moves the probe carrier 2 by means of a rack 9 and a pinion 8.

Figure 2:
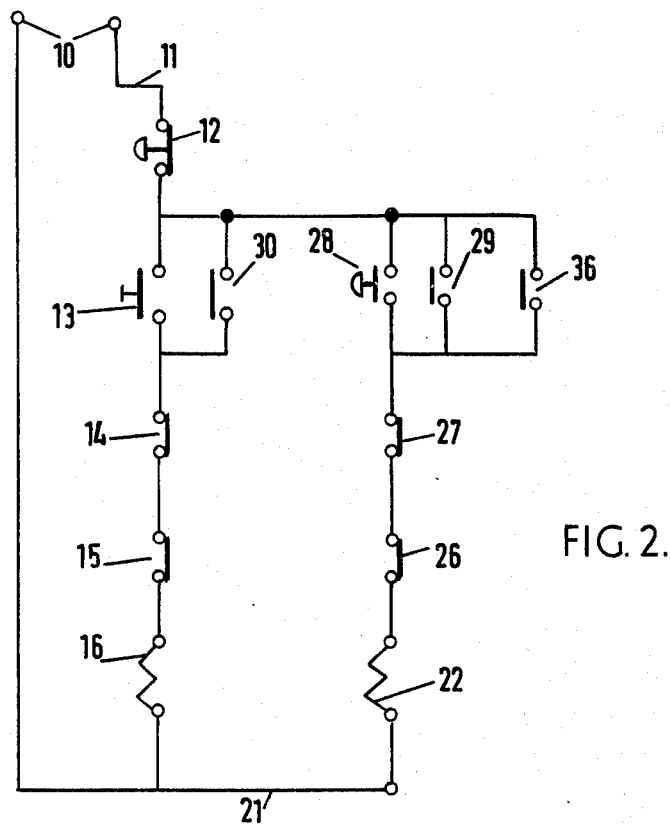
FIGS. 2 to 4 illustrates control circuitry for controlling the descent and return movement of the probe.
Figure 3:
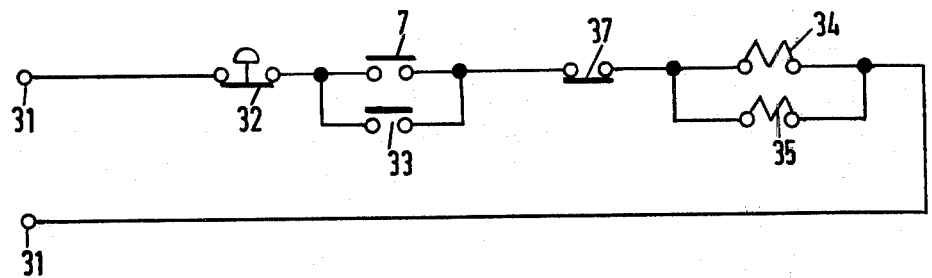
Figure 4:
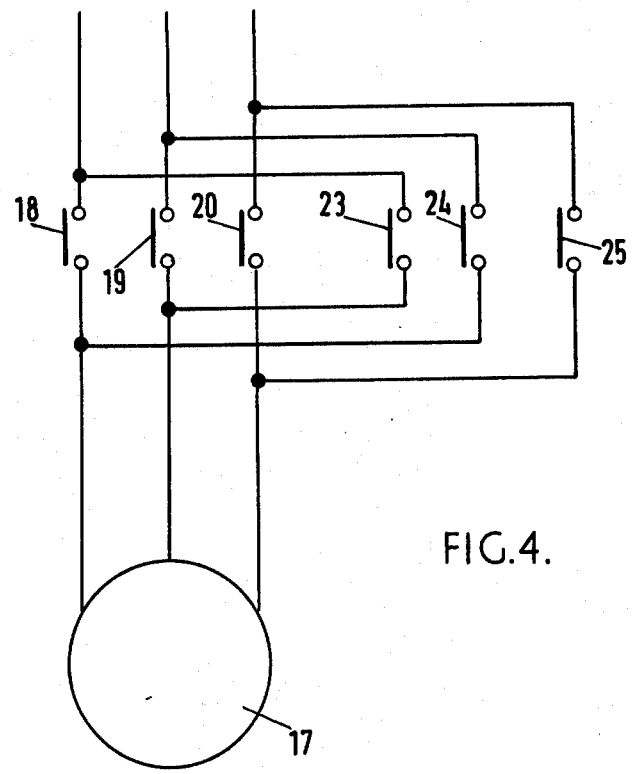

A control device for controlling the descent and the return movement of the probe, as well as its residence time at a given depth, is shown in FIGS. 2 to 4.

The terminals 10 of an electrical supply network, for example of 220 volts, are indicated. One circuit 11 connects in series: a manually operable switch 12; a pushbutton 13 controlling the descending movement of the probe; a contact 14 which is open when a relay 22 controlling the return (ascent) is energized; a normally closed contact 15; and a relay 16 which, when energized, causes (through three contacts 18, 19 and 20) rotation of the motor 17 (FIG. 4) in the direction corresponding to the descent of the probe. In a parallel circuit 21, there are provided in series: the relay 22 which, when energized, causes (through contacts 23, 24 and 25) the rotation of the motor 17 in the direction corresponding to the return of the probe; a contact 26 limiting the upward return movement; a contact 27 which is closed when the relay 16 is not energized; and a push-button 28 for manually controlling the return of the probe.

A holding contact 29 is connected in parallel with the push-button 28 and is closed when the relay 22 is energized. A time contact 36 is also connected in parallel with the push-button 28 and controls the operation of an automatic control device (FIG. 3) controlling the movement of the probe. A holding contact 30, which is closed when the relay 16 is energized, is connected in parallel with the push-button 13.

The automatic control device controlling the movements of the probe comprises (FIG. 3): a push-button 32 for connecting the device to the electrical supply network (terminals 31); the micro-switch 7 (see FIG. 1) coupled to the automatic stop diaphragm 6; a holding contact 33 connected in parallel with the micro-switch 7 and closed when a relay 34 is energized; a contact 37 for resetting timing to zero; the relay 34 which controls the stopping of the descent of the probe; and a timed relay 35 connected in parallel with the relay 34 and controlling the return of the probe.

The apparatus operates as follows.

Initially the probe is located at its uppermost position above the molten metal. The switch 12 and the contacts 14 and 15 are closed.

The operator presses the button 13, thereby closing the energization circuit of the relay 16 which controls the following operations: (a) closing the contact 30, thereby ensuring the holding of the supply of the circuit 11; (b) opening of the contact 27, thereby preventing the relay 22 from being energized at the same time as the relay 16; (c) closing the contacts 18, 19 and 20, thereby applying voltage to the motor 17 and causing it to rotate in the direction corresponding to the descent of the probe.

When the lower end of the cardboard ferrule 4 reaches the upper surface of the molten metal, the diaphragm 6 is actuated by the gas pressure generated in the tube 3 owing to the combustion of the end of the ferrule 4. The diaphragm 6 closes the micro-switch 7 and the circuit (FIG. 3) connected to the terminals 31 energizes the relays 34 and 35 through the contacts 32 and 37, which are closed at this time. The relay 34 upon being energized closes the contact 33, serving to hold the supply of the relay 34 and opens the contact 15, thereby de-energizing the relay 16 and stopping the rotation of the motor 17 and thus the descent of the probe. (It will be appreciated that there is an unavoidable delay between contact of the ferrule 4 with the molten metal and stopping of the descent of the probe; this should be taken into account when setting the height of the ferrule above the probe.)

The energization of the timed relay 35 results in the closing of the contact 36 after a predetermined time period. The closing of the contact 36 results in the closing of the energization circuit of the relay 22 through the contact 27 (closed upon de-energizing of the relay 16) and the contact 26 (which will be opened only at the end of the upward movement).

The energization of the relay 22 results in the following operations: (a) opening of the contact 14, thereby preventing any untimely re-energization of the relay 16; (b) opening of the contact 37, thereby de-energizing the relays 34 and 35; (c) closing of the contacts 23, 24 and 25, thereby applying voltage to the motor 17 in order to cause it to rotate in the direction corresponding to the return movement of the probe, (d) closing of the contact 29 while maintaining the supply connected to the circuit 21 and, as a consequence, energization of the relay 22 after the contact 36 has been re-opened upon de-energization of the relay 35.

The return movement of the probe continues until the end of the upward movement, where the contact 26 is opened, which results in the de-energization of the relay 22, which in turn results in the closing of the contact 14 and the opening of the contacts 23, 24 and 25. The device is now in the starting condition again.

I claim:

1. An apparatus for testing molten metal by lowering a measuring or sampling probe to a desired depth in the molten metal, the apparatus comprising: a probe; a probe carrier; means for lowering and raising the probe carrier; and a contact detector which emits a pneumatic signal when the detector comes into contact with the molten metal, the detector being fixed on the probe carrier at a distance above the probe and comprises a hollow body of material which burns on contact with molten metal, the pneumatic signal being produced by the pressure created in the hollow body by the gaseous products of combustion of the material.

2. The apparatus as claimed in claim 1, further comprising automatic means for stopping the lowering of the probe carrier, the automatic stopping means being actuated by the pneumatic signal emitted by the contact detector.

3. The apparatus as claimed in claim 1, in which the hollow body is a tube whose axis extends in the direction of motion of the probe carrier.

4. The apparatus as claimed in claim 1, further comprising automatic means for starting the raising of the probe carrier when a predetermined delay period has elapsed after stopping of the lowering of the probe.

5. The apparatus as claimed in claim 1, including: (a) an electric motor arranged to drive the raising and lowering means; (b) a first delay controlling the starting of the motor so that it rotates in one direction to lower the probe; (c) a second relay controlling the starting of the motor so that it rotates in the opposite direction to raise the probe; (d) a third relay controlling the stopping of the motor; and (e) a timed relay controlling the second relay so as to start the motor, in the opposite direction, after a predetermined delay period has elapsed after stopping; and in which:

i. upon actuation of the first relay, the motor commences rotation to lower the probe;
   ii. upon emission of the pneumatic signal by the contact detector, the third relay is actuated to stop the motor and to actuate the timed relay; and
   iii. the timed relay, at the end of the predetermined delay period, actuates the second relay, whereby the motor commences rotation to raise the probe.

* * * * *